(12) United States Patent
Ueda et al.

(10) Patent No.: US 6,787,148 B1
(45) Date of Patent: Sep. 7, 2004

(54) CHEMICAL PEELING AGENT

(76) Inventors: Setsuko Ueda, 2-3, Kasumigaoka 3-chome, Higashi-ku, Fukuoka-shi, Fukuoka (JP); Kaori Ueda, 2-3, Kasumigaoka 3-chome, Higashi-ku, Fukuoka-shi, Fukuoka (JP)

( * ) Notice: Subject to any disclaimer, the term of this patent is extended or adjusted under 35 U.S.C. 154(b) by 0 days.

(21) Appl. No.: 10/069,906
(22) PCT Filed: Sep. 6, 2000
(86) PCT No.: PCT/JP00/06040
§ 371 (c)(1), (2), (4) Date: Feb. 22, 2002
(87) PCT Pub. No.: WO01/17487
PCT Pub. Date: Mar. 15, 2001

(30) Foreign Application Priority Data

Sep. 6, 1999 (JP) .............................. 11-251802
May 25, 2000 (JP) ....................... 2000-155339

(51) Int. Cl.⁷ ............................ A61K 7/00; A61K 31/05
(52) U.S. Cl. ....................... 424/401; 514/731; 514/846; 514/848
(58) Field of Search .............................. 424/78.03, 401; 514/731, 846, 848

(56) References Cited

U.S. PATENT DOCUMENTS 6,180,669 B1 * 1/2001 Tamarkin ..................... 514/548

FOREIGN PATENT DOCUMENTS

| EP | 55 035 025 | | 3/1980 |
|----|----|----|----|
| EP | 0196632 | * | 8/1986 |
| EP | 0395 329 | | 10/1990 |
| GB | 754867 | * | 8/1956 |
| GB | 754 867 | | 8/1956 |
| JP | 55-35025 | * | 3/1980 |
| JP | 11130634 | | 5/1999 |
| JP | 11-130634 | | 5/1999 |
| JP | 11-236707 | | 9/1999 |
| JP | 11263707 | | 9/1999 |
| JP | 00086440 | | 3/2000 |
| JP | 2000-86440 | | 3/2000 |
| JP | 00219618 | | 8/2000 |
| JP | 2000-219618 | | 8/2000 |
| WO | 97/28786 | | 8/1997 |
| WO | 98/20834 | | 5/1998 |

* cited by examiner

Primary Examiner—Barbara P. Badio
(74) Attorney, Agent, or Firm—Jordan and Hamburg LLP

(57) ABSTRACT

The chemically peeling agent contains a component (A) having the following general formula:

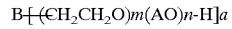

B—[(CH₂CH₂O)$m$(AO)$n$-H]$a$ (wherein B is an alcohol residue;
AO is an alkylene-oxy group having 3 to 18 carbon atoms;
a is an integer of 1 or more;
m is an integer of 4 or more; and
n is 0 or an integer of 1 or more;
provided that a molar amount m of the oxidized ethylene to be added is a value that amounts to 40% or more of the entire molecular weight of an ethylene oxide chain moiety)
and a phenol compound (B) formulated in an amount ranging from 10% to 30% by weight.

8 Claims, No Drawings

CHEMICAL PEELING AGENT

This application is a 371 of PCT/JP00/06040 filed Sep. 6, 2000.

TECHNICAL FIELD

The present invention relates to a chemically peeling agent adapted to remove wrinkles, spots (pigmentation such as geriatric pigment spots) and a somber color on the skin, to treat pimples, and to improve a greasy skin. The term "chemically peeling agent" referred to in this description is intended to mean a chemically peeling agent for use as medicine or cosmetics.

In the West, removal of wrinkles, spots and so on is considered as one of methods for medical treatments. A treatment method that is generally adopted at hospitals of dermatology, orthopedics, or cosmetic surgery in the western countries, involves pasting the skin with an aqueous solution of different concentrations of a chemically peeling agent, including trichloroacetic acid (TCA), phenol and so on, for an appropriate duration of time to artificially make a chemical burn (corrosion) and thereafter to reproduce normal cells on the skin in a natural way.

This treatment with such chemically peeling agents, however, is effective for white people, it may cause the skin of Asian people problems with side effects including red spots, pigmentation, scars and so on after operation.

Recently, it has been found that α-hydroxy acid (AHA) is relatively safe and it is effective for the peeling treatment for Asian people. This treatment has now been conducted as a general treatment method. The effects and the side effects to be produced by this method, however, greatly depend upon the concentration and pH of AHA, so that it suffers from the difficulty that this treatment method requires experienced skills.

More recently, the treatment with a solution of salicylic acid in an alcohol has been adopted in the U.S. and it has been found to be effective for white people. This treatment method, however, causes Asian people problems with severe side effects including, for example, flare or pain during treatment and pigmentation after treatment.

As a result of extensive and long-lasting research, it was found by the present inventor that, although an agent containing salicylic acid in polyethylene glycol cannot be absorbed through the skin so that it has been considered to be ineffective for the treatment of skin diseases, a mixture of salicylic acid with polyethylene glycol allows salicylic acid to be sustained in the polyethylene glycol and retained in the horny layer without penetrating into a sebaceous matter at a high concentration and to strongly peel off the horny layer only without causing any systemic side effects. Further, it was found that a mixture of a phenol compound, such as phenol or resorcinol, with a polyethylene glycol or an equivalent compound could exhibit the effects similar to the mixture of salicylic acid with the polyethylene glycol.

The present invention has been completed on the basis of these findings and has the object to provide a chemically peeling agent that does not cause any side effects including red spots, pigmentation and scars after operation, refreshes the skin (removing fine wrinkles and providing the skin with flexibility), removes spots, and improve a somber color on the skin. Further, the chemically peeling agent can treat pimples and improve a greasy skin.

DISCLOSURE OF INVENTION

In order to achieve the object as described above, the present invention provides a chemically peeling agent comprising a component (A) having the following general formula:

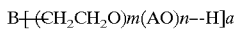

(wherein B is an alcohol residue;
AO is an alkylene-oxy group having 3 to 18 carbon atoms;
a is an integer of 1 or more;
m is an integer of 4 or more; and
n is 0 or an integer of 1 or more;
provided that a molar amount $\underline{m}$ of the oxidized ethylene to be added is a value that amounts to 40% or more of the entire molecular weight of an ethylene oxide chain moiety)
and a phenol compound (B) formulated in an amount ranging from 10% to 30% by weight.

The component (A) to be used for the present invention may be represented by the above general formula.

In the above general formula, the alcohol to be represented by reference symbol B is intended to mean a mono-valent alcohol Including, for example, an alkyl alcohol such as methanol, ethanol, butanol, lauryl alcohol, myristyl alcohol, palmityl alcohol, stearyl alcohol, cetyl alcohol, etc., and an alkenyl alcohol such as linoleyl alcohol, palmitoyl alcohol, oleyl alcohol, etc., a di-valent alcohol such as ethylene glycol, propylene glycol, etc., a tri-valent alcohol such as glycerin, trimethylol propane, triethanol amine, etc., a tetra-valent alcohol such as pentaerythritol, diglycerin, etc. There may also be used other poly-valent alcohols such as sorbitol, polyglycerin and so on.

The alkylene-oxy group having 3 to 18 carbon atoms, as referred to by reference symbol AO, may include, for example, propylene-oxy, butylene-oxy, tetrahydrofuran, α-olefin-oxy, and so on. The alkylene-oxy groups having 3 and 4 carbon atoms, such as oxido-propylene, oxido-butylene and tetrahydrofuran, are preferred.

In the above general formula, reference symbol "a" is an integer of 1 or more. When the alcohol to be used for the present invention is a mono-valent alcohol, the reference symbol "a" is 1. When the alcohol to be used therefor is a di-valent alcohol, the reference symbol "a" is 2. Likewise, when the alcohol to be used therefor is a tri-valent alcohol, the reference symbol "a" is 3. Further, when the alcohol to be used therefor is a poly-valent alcohol, the reference symbol "a" is the integer corresponding to the valence of the alcohol used.

In the above general formula, reference symbol "m" is intended to mean an average molar amount of ethylene oxide to be added. The number of a polymerization chain of the ethylene oxide has to be at least 4.

Reference symbol "n" is intended to mean an average molar amount of an oxidized alkylene to be added. The number of a polymerization chain of the oxidized alkylene is zero or 1 or more.

The manner of polymerization of the ethylene oxide and the alkylene oxide is random or block polymerization.

The molar amount $\underline{m}$ of the ethylene oxide to be added is set to amount to 40% or more of the entire molecular weight of the ethylene oxide chain. This setting is based on the fact that, if the molar amount $\underline{m}$ of the ethylene oxide to be added would be less than the above molar amount, the phenol compound such as salicylic acid would become unlikely to be sustained in the polyethylene glycol derivative.

The component (A) may be synthesized in a conventional manner, for example, by reacting the ethylene oxide and the alkylene oxide with the alkyl alcohol or the alkenyl alcohol under an inert gas such as nitrogen or the like in the presence of a basic catalyst such as sodium hydroxide, potassium hydroxide or the like or an acidic catalyst such as boron tetrafluoride, tin tetrachloride or the like.

Specific examples of the compounds (A) may include, for example, a polyethylene glycol and a derivative thereof, a polyoxyethylene polyoxypropylene glycol and a derivative thereof, and a polyoxyethylene long-chain alkyl ether and a polyoxyethylene long-chain alkenyl ether to be used as a non-ionic surfactant. Among these examples, the polyethylene glycol is listed as trade name "Macrogol" in the Japanese Pharmacopoeia and the Regulations of Medicinal Additives. Likewise, a block copolymer of ethylene oxide or propylene oxide is listed as a poloximer therein. The phenol compound to be added as the main component can be sustained in those compounds and retained in the horny layer without penetrating into a sebaceous matter at a high concentration. Therefore, these compounds can preferably be used because they have no risk of causing any systemic side effects and can peel only the horny layer off. These compounds can be used singly or in combination of two or more.

As the phenol compound (B) to be used for the present invention, there may be mentioned phenol, resorcinol, salicylic acid and so on.

Among the phenol compounds (B), salicylic acid is preferred. The phenol compounds may be used singly or in combination of two or more.

The amount of the phenol compound to be added may be in the range of from 10 to 30% by weight. When the phenol compounds are to be combined with two kinds or more, the amounts of the compounds are to be appropriately selected within the scope so as to effectively peel the horny layer off and cause no side effects.

The chemically peeling agent according to the present invention may preferably include an alkyl acrylate-methacrylate copolymer in the amount of from 0.1% to 5% by weight as a gelling agent or a viscosity-adjusting agent in order to prevent the softening of the product particularly in the summer season.

To the chemically peeling agent according to the present invention, there may be added various conventional additives for use with an ointment or cosmetics, which do not interfere with the efficacy or impose any influence upon the efficacy of the chemically peeling agent. Such additives may include, for example, an aromatic, a surfactant, a preservative, an anti-oxidant, a moisturizing agent, and so on, and they are to be used in an appropriate amount that does not reduce the efficacy of the chemically peeling agent. In addition, vitamin A acid may be added. Moreover, the addition of the surfactant and so on can preferably improve the efficacy of the agent.

The chemically peeling agent according to the present invention may be prepared in a conventional way, for example, by mixing the component (A) in a molten state with the component (B) at ambient temperature or elevated temperature or under addition of pressure and adding various additives thereto as needed.

The chemically peeling agent according to the present invention may be applied, for example, by pasting the chemically peeling agent on the skin and wiping the agent out from the skin after a given period of time. The application of this agent can serve as removing the epidermis (mainly the cuticle) of the skin and imposing influences upon the cells of the stratum spinosum epidermidis and the stratum basale epidermidis of the epidermis, thereby causing the reproduction of the fibroblast of the corium. The aged corium portion can be replaced with the reproduced fibroblast to induce the skin-restoring effects. This can remove wrinkles on the skin and restore the elastic power in the skin. At the same time, the cuticle of the hair follicle is also peeled off and the accumulated cuticle can be removed, thereby curing pimples. The disinfecting effects of the main components of the chemically peeling agent can synergistically act on the pimples and improve the greasy skin, too.

As the chemically peeling agent according to the present invention can re-structure the corium of the skin by peeling the horny layer off and reproducing the fibroblast in the corium, melanin withering the curium can be removed from the focus as time elapses. Further, the fibrous tissues reproduced in layers on top of melanocyte of a neoblast so that bluish to brownish color in hue can also be masked when looked at an appearance. Therefore, chromatosis induced by those causes can also be cured so that spots and dark or somber color on the skin can be caused to disappear.

The duration for pasting the chemically peeling agent may be preferably set to be for from 3 minutes to 20 minutes, although it is not restricted to the particular period of time. It can be appropriately selected from the duration of time that does not cause any side effects and can effectively produce the peeling effects.

It is to be noted herein that, if the phenol compound such as salicylic acid is applied at a low concentration, the chemically peeling agent can be preferably applied to the skin after removal of the cuticle, whereby the cuticle remaining in the hair follicle or in the skin can be removed effectively without causing any side effects.

BEST MODES FOR CARRYING OUT THE INVENTION

The present invention will be described in more detail by way of examples. In the following description, examples are described in which polyethylene glycol is used as the component (A). It is to be noted herein, however, that the use of the other components (A) can also exhibit the effects substantially identical to or similar to the examples where polyethylene glycol is used as the component (A). Further, it is to be noted herein that, although polyethylene glycol having a molecular weight of 1,500 is used in each of the following examples, a polyethylene glycol having a molecular weight ranging from 1,500 to 20,000 can also be used preferably from the point of view of penetration of the main component into the skin tissue and the unlikelihood of an occurrence of side effects or from other reasons. Moreover, such polyethylene glycols may also be used singly or in combination of two or more while adjusting viscosity, penetrating ability and other properties.

EXAMPLE 1

A chemically peeling agent was prepared by mixing 90% by weight of polyethylene glycol 1500 with 10% by weight of salicylic acid.

A face of each of 20 women in the sixties was pasted with the chemically peeling agent and the agent was wiped out in 20 minutes. The pasting was carried out once a month for three months. It should be noted herein that salicylic acid used herein is the one that is generally used as a softening agent for the horny layer of the skin or a disinfectant.

An observation was conducted by means of a digital camera. The observation revealed a slight disappearance of shallow wrinkles and a slight rise in hue and brightness for all the persons under test. An observation by a scanning electronic microscope of cheek replica indicates a slight disappearance of wrinkles in the skin.

Further, no side effects including, for example, red spots, pigmentation, scars and so on were recognized for all the persons under test.

It was also found that the agent containing salicylic acid in the concentration of 10% by weight or less could remove the horny layer left in the hair follicle and the skin effectively without causing any side effects, when the skin was pasted with the agent after removal of the horny layer.

EXAMPLE 2

A chemically peeling agent was prepared by mixing 80% by weight of polyethylene glycol 1500 with 20% by weight of salicylic acid.

A face of each of 50 women in the sixties was pasted with the chemically peeling agent and the agent was wiped out in 10 minutes. The pasting was carried out once a month for three months.

An observation was conducted by means of a digital camera and the observation revealed a disappearance of shallow wrinkles and a rise in hue and brightness for all the persons under test. An observation by a scanning electronic microscope of cheek replica indicates an apparent disappearance of wrinkles in the skin. A comparison before and after the treatment with the chemically peeling agent indicated an increase of the water content in the horny layer, a rise in the amount of vaporization of moisture through the skin, and improvements in development of the skin (when observed with a cuticle meter).

Further, no side effects including, for example, red spots, pigmentation, scars and so on were recognized for all the persons under test.

EXAMPLE 3

A chemically peeling agent was prepared by mixing 70% by weight of polyethylene glycol 1500 with 30% by weight of salicylic acid.

A face of each of 10 women in the sixties was pasted with the chemically peeling agent and the agent was wiped out in 5 minutes. The pasting was carried out once a month for three months.

An observation was conducted by means of a digital camera and the observation revealed a disappearance of shallow wrinkles and a rise in hue and brightness for all the persons under test. An observation by a scanning electronic microscope of cheek replica indicates an apparent disappearance of wrinkles in the skin. A comparison before and after the treatment with the chemically peeling agent indicated a light increase of the water content in the horny layer, a light rise in the amount of vaporization of moisture through the skin, and improvements in development of the skin (when observed with a cuticle meter).

Further, no side effects including, for example, red spots, pigmentation, scars and so on were recognized for all the persons under test.

EXAMPLE 4

A chemically peeling agent was prepared by mixing 90% by weight of polyethylene glycol 1500 with 10% by weight of phenol.

A face of each of 10 women in the sixties was pasted with the chemically peeling agent and the agent was wiped out in 3 minutes. The pasting was carried out once a month for three months.

An observation was conducted by means of a digital camera and the observation revealed a disappearance of shallow wrinkles and a rise in hue and brightness for all the persons under test. An observation by a scanning electronic microscope of cheek replica indicates an apparent disappearance of wrinkles. In the skin. A comparison before and after the treatment with the chemically peeling agent indicated a light increase of the water content in the horny layer, a light rise in the amount of vaporization of moisture through the skin, and improvements in development of the skin (when observed with a cuticle meter).

Further, no side effects including, for example, red spots, pigmentation, scars and so on were recognized for all the persons under test.

It was also found that the agent containing phenol in the concentration of 5% by weight or less could remove the horny layer left in the hair follicle and the skin effectively without causing any side effects, when the skin was pasted with the agent after removal of the horny layer.

EXAMPLE 5

A chemically peeling agent was prepared by mixing 90% by weight of polyethylene glycol 1500 with 10% by weight of resorcinol.

A face of each of 10 women in the sixties was pasted with the chemically peeling agent and the agent was wiped out in 10 minutes. The pasting was carried out once a month for three months.

An observation was conducted by means of a digital camera and the observation revealed a disappearance of shallow wrinkles and a rise in hue and brightness for all the persons under test. An observation by a scanning electronic microscope of cheek replica indicates an apparent disappearance of wrinkles in the skin.

A comparison before and after the treatment with the chemically peeling agent indicated a light increase of the water content in the horny layer, a light rise in the amount of vaporization of moisture through the skin, and improvements in development of the skin (when observed with a cuticle meter).

Further, no side effects including, for example, red spots, pigmentation, scars and so on were recognized for all the persons under test.

It was also found that the chemically peeling agent containing resorcinol in the concentration of less than 10% by weight In polyethylene glycol could remove the horny layer left in the hair follicle and the skin effectively without causing any side effects, when the skin was pasted with the agent after removal of the horny layer.

INDUSTRIAL UTILIZABILITY

The chemically peeling agent according to the present invention can retain the phenol compound in the component (A) and sustain the phenol compound in the horny layer without penetrating in the sebaceous matter at a high concentration so that it can strongly peel only the horny layer off without causing any risk of an occurrence of systemic side effects. Therefore, the chemically peeling agent according to the present invention can effectively remove wrinkles, spots (pigmentation such as geriatric pigment spots) and a somber color on the skin. It can also be used for treatment of pimples and improvements in the greasy skin.

For the present invention, the polyethylene glycol is used as a substrate so that it can serve as adhering to the skin well upon pasting the skin with the agent without causing any irritating. Further, the agent can be easily dissolved in water so that it can be readily washed away with water. Therefore, the chemically peeling agent according to the present invention can be used effectively and safely without requiring experienced skills.

What is claimed is:

1. A chemically peeling agent consisting of from 90 to 70% by weight of polyethylene glycol and from 10 to 30% by weight of salicylic acid.

2. A chemically peeling agent consisting of 90 to 50% by weight of polyethylene glycol and from 10 to 50% by weight of phenol.

3. A chemically peeling agent consisting of from 90 to 50% by weight of polyethylene glycol and 10 to 50% by weight of resorcinol.

4. A chemically peeling agent consisting of from 90 to 70% by weight of polyethylene glycol and 10 to 30% by weight of a compound selected from the group consisting of salicylic acid, phenol and resorcinol.

5. A method of chemically peeling human skin consisting of applying thereto a chemically peeling agent according to claim 1.

6. A method of chemically peeling human skin consisting of applying thereto a chemically peeling agent according to claim 2.

7. A method of chemically peeling human skin consisting of applying thereto a chemically peeling agent according to claim 3.

8. A method of chemically peeling human skin consisting of applying thereto a chemically peeling agent according to claim 4.

* * * * *